… [11] Patent Number: 5,384,323
[45] Date of Patent: Jan. 24, 1995

[54] STABILIZED DOPAMINERGIC COMPOSITIONS

[75] Inventors: Joachim Bolz, Heidelberg; Atilla Batu, Darmstadt; Herbert Seeger, Modautal, all of Germany

[73] Assignee: Merck Patent Gesellschaft mit Beschrankter Haftung, Darmstadt, Germany

[21] Appl. No.: 989,857

[22] Filed: Dec. 14, 1992

[30] Foreign Application Priority Data

Dec. 14, 1991 [DE] Germany ............................ 4141268

[51] Int. Cl.$^6$ ........................................... A61K 31/435
[52] U.S. Cl. ................................................... 514/339
[58] Field of Search ................................. 514/343, 339

[56] References Cited

U.S. PATENT DOCUMENTS 4,914,114  4/1990  Hausberg et al. .................... 514/339
5,073,380  12/1991  Babu et al. ............................ 424/472

OTHER PUBLICATIONS

Asghar et al., Chemical Abstracts CA102(18):154746j, 1983.

Klimke et al., Biosis BA93:33126, 1991.

*Primary Examiner*—Raymond J. Henley, III
*Assistant Examiner*—William R. A. Jarvis
*Attorney, Agent, or Firm*—Millen, White, Zelano & Branigan

[57] ABSTRACT

The invention relates to a pharmaceutical composition containing as the active ingredient a compound of formula I:

wherein
  R is OH or COOH,
  or one of its pharmacologically acceptable salts, in the form of an inclusion in pregelatinized starch, which can contain at least one other adjunct.

8 Claims, No Drawings

STABILIZED DOPAMINERGIC COMPOSITIONS

BACKGROUND OF THE INVENTION

The invention relates to a novel pharmaceutical composition containing as the active ingredient a compound of formula I:

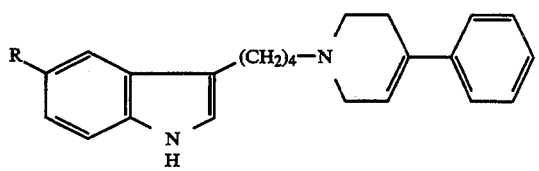

wherein
R is OH or COOH,
or one of its pharmacologically acceptable salts, in the form of an inclusion in pregelatinized starch, which can contain at least one other adjunct as an active or inactive component.

The compounds of formula I include roxindol (I, R=OH; compare European patent 281 608 which corresponds to U.S. Pat. No. 4,914,114) and carmoxirol (I, R=COOH; compare European patent 144 012 which corresponds to U.S. Ser. No. 07/674,635 now U.S. Pat. No. 5,069,794). They can also be used in the form of their pharmacologically acceptable salts, especially their acid addition salts or, in the case of carmoxirol, also their salts with bases. Acid addition salts which can be used are salts with inorganic acids, for example with sulfuric acid, nitric acid, hydrohalic acids such as hydrochloric acid or hydrobromic acid, phosphorus acids such as orthophosphoric acid, and sulfamic acid, and salts with organic acids, especially with aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, furamic acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methdne- or ethane-sulfonic acid, ethanedisulfonic acid, 2-hydroxyethanesulfonic acid, benzenesulfonic acid, p-toluenesulfonic acid, naphthalene-monosulfonic and -disulfonic acids and laurylsulfuric acid. Roxindol is preferably used in the form of the methanesulfonate and carmoxirol in the form of the hydrochloride.

For carmoxirol, possible salts with bases are especially the sodium, potassium, magnesium, calcium and ammonium salts, as well as substituted ammonium salts, for example the dimethyl-, diethyl- or diisopropylammonium, monoethanol-, diethanol- and triethanolammonium, cyclohexylammonium, dicyclohexylammonium and dibenzylethylenediammonium salts.

Roxindol is a dopamine agonist and is used as a neuroleptic. Carmoxirol is a dopaminergic hypotensive.

However, attempts to prepare durable and reproducibly stable pharmaceutical formulations of roxindol and carmoxirol, especially for oral administration, met with considerable difficulties. Thus this object could not be achieved with quite a number of conventional methods: preparation of granules, for example with lactose hydrate, mannitol or microcrystalline cellulose as the filler, especially also using solutions of cellulose ethers or gelatin; inclusions in gelatin with subsequent addition of fillers; absorption of he active ingredients from solution, for example on to lactose hydrate, mannitol or microcrystalline cellulose; and trituration of the active ingredients with lactose hydrate or pregelatinized maize starch.

Attempts to stabilize said formulations with antioxidants such as ascorbic acid, tocopherol or tocopherol derivatives, or with citric acid, did not give the desired result either.

SUMMARY OF THE INVENTION one of the objects of the invention was to find a stable pharmaceutical composition for said active ingredients.

Upon further study of the specification and appended claims, further objects and advantages of this invention will become apparent to those skilled in the art.

It has been found, surprisingly, that inclusions of these active ingredients in pregelatinized starch satisfy the necessary demands on durability and stability, in contrast to the other formulations mentioned. Inclusion is not meant to imply a particular limitation but simply to indicate that the active ingredient is embedded, e.g., by absorption or adsorption in the pregelatinized starch.

Pregelatinized starch, especially pregelatinized maize starch, but also potato, wheat, rice or tapioca starch, are known and commercially available (e.g., Colorcon's STARCH 1500 TM). Because of its tendency to swell, pregelatinized starch is not normally used as an excipient for active ingredients in similar cases. Its use for the preparation of the formulations according to the invention therefore means that a prejudice among those skilled in the art has been overcome.

A preferred commercial product is a pregelatinized maize starch with the following characteristics:
Particle size: at least 90% <150 μ
Bulk volume: 1.6 ml/g
Tamped volume: 1.3 ml/g
Fraction soluble in cold water: 10–20%
Loss on drying: maximum 14%
pH of a dispersion in water: 4.5–7

The inclusion according to the invention can contain one or more other adjuncts, possible examples being: lubricants such as magnesium or calcium stearate, calcium behenate or talc; binders such as cellulose, especially microcrystalline cellulose; flow regulators such as highly disperse silicon dioxide; disintegrating agents such as the sodium salts of carboxymethyl cellulose or carboxymethyl starch, or polyvinylpyrrolidone; and fillers such as lactose or dextrins.

The inclusion preferably contains 0.1 to 5, especially 0.5 to 2 percent by weight of active ingredient, 70 to 99.9, especially 80 to 99 percent by weight of pregelatinized starch and 0 to 29.9, especially 0.3 to 20 percent by weight of other adjuncts.

The inclusion can be prepared as indicated below and converted to conventional forms for oral administration, especially tablets or capsules, but also pellets.

Accordingly the invention further relates to a novel process for the preparation of a pharmaceutical formulation according to claim 1, characterized in that (a) a solution of the active ingredient is absorbed on to pregelatinized starch (or on to a mixture of pregelatinized starch and at least one other adjunct), or (b) the active ingredient in micronized form is mixed with pregelatinized starch (or with a mixture of pregelatinized starch and at least one other adjunct) and water or a water/alcohol mixture is added, the mixture obtained according to (a) or (b) is kneaded, if necessary, and then sieved and dried and, if appropriate, the resulting inclusion is converted to tablets or capsules in conventional manner.

The active ingredient is preferably dissolved in ethanol or in a mixture of ethanol and water or acetone and water.

It is advantageous for all the process steps to be carried out at temperatures of between 10° and 40°, preferably of between 20° and 30°.

If desired, the tablets obtained can be lacquered in conventional manner or provided with a table coating, which may be resistant to gastric juices or be a retardant in some other way.

The formulation according to the invention is stable especially to oxidative decomposition and permits rapid release of the active ingredient (if no importance is attached to retardation).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German No. P 41 41 268.0, are hereby incorporated by reference.

EXAMPLES

EXAMPLE 1

Hard gelatin Capsules 1 mg 200 g of roxindol methanesulfonate are dissolved at 30° in a mixture of 3 l of ethanol and 3 l of water. 27,725 g of pregelatinized maize starch are placed in a kneader and the solution obtained is applied to the maize starch. The mass is kneaded and passed through a granulation sieve (1 mm mesh). The resulting granules are dried under reduced pressure to a water content of 5-9%, sieved again (0.8 mm mesh) and mixed with 75 g of magnesium stearate and the resulting product is filled into hard gelatin capsules (size 4; empty weight of one capsule 40 mg). Each capsule contains 1 mg of roxindol methanesulfonate, 138.625 mg of pregelatinized starch and 0.375 mg of magnesium stearate.

Capsules which each contain 1 mg of carmoxirol hydrochloride in place of the roxindol methanesulfonate as the active ingredient are obtained analogously.

EXAMPLE 2

Lacquered tablets 2.5 mg 50 g of roxindol methanesulfonate are dissolved at 30° in a mixture of 300 ml of ethanol and 300 ml of water. 2330 g of pregelatinized maize starch and 400 g of microcrystalline cellulose are placed in a kneader and the solution obtained is applied to the starch and cellulose. The subsequent procedure is analogous to Example 1, the granules are then mixed with 20 g of magnesium stearate and the mixture is compressed to tablet cores (7 mm diameter, 6 mm radius of curvature) each composed of 2.5 mg of roxindol, 116.5 mg of pregelatinized starch, 20 mg of microcrystalline cellulose and 1 mg of magnesium stearate. The cores are then lacquered in conventional manner in a coater using a suspension composed of 14 g of titanium dioxide, 20 g of yellow iron oxide, 0.04 g of red iron oxide, 36 g of hydroxypropyl methyl cellulose, 9 g of polyethylene glycol 400, 300 ml of ethanol and 300 ml of water. The resulting lacquered tablets are dried at 30°.

Lacquered tablets which each contain 2.5 mg of carmoxirol hydrochloride in place of the roxindol methanesulfonate as the active ingredient are obtained analogously.

EXAMPLE 3

Hard gelatin capsules 2 mg 40 g of carmoxirol hydrochloride are mixed first with 500 g and then with a further 2245 g of pregelatinized maize starch, a mixture of 400 ml of ethanol and 400 ml of water is added and the resulting mixture is kneaded for 10 minutes. The moist mass is passed through a granulation sieve (1 mm mesh). The resulting granules are dried under reduced pressure to a water content of 5-9%, sieved again (0.8 mm mesh) and mixed with 5 g of highly disperse silicon dioxide and 10 g of magnesium stearate and the resulting product is filled into hard gelatin capsules (size 4). Each capsule contains 2 mg of carmoxirol hydrochloride, 137.25 mg of pregelatinized starch, 2.5 mg of silicon dioxide and 5 mg of magnesium stearate.

Capsules which each contain 2 mg of roxindol methanesulfonate in place of the carmoxirol hydrochloride as the active ingredient are obtained analogously.

EXAMPLE 4

Lacquered tablets 2 mg 40 g of micronized carmoxirol hydrochloride are mixed with 500 g of pregelatinized potato starch, a further 1445 g of pregelatinized potato starch and 400 g of microcrystalline cellulose are than added and the ingredients are mixed again. This mixture is treated with a mixture of 400 ml of ethanol and 400 ml of water, kneaded thoroughly for 10 minutes, passed through a granulation sieve (1 mm mesh), dried under reduced pressure to a water content of 5.9%, sieved again (0.8 mm mesh) and mixed with 5 g of highly disperse silicon dioxide and 10 g of magnesium stearate and the resulting mixture is compressed to tablet cores (7 mm diameter, 6 mm radius of curvature) each composed of 2 mg of carmoxirol hydrochloride 97.25 mg of pregelatinized potato starch, 20 mg of microcrystalline cellulose, 0.25 mg of highly disperse silicon dioxide and 0.5 mg of magnesium stearate. The cores are then lacquered analogously to Example 2.

EXAMPLE 5

Lacquered tablets 5 mg

Lacquered tablets whose cores have the following composition are obtained analogously to Example 2: 5 mg of roxindol methanesulfonate, 200 mg of pregelatinized rice starch, 73 mg of microcrystalline cellulose and 2 mg of magnesium stearate.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modification of the invention to adapt it to various usages and conditions.

What is claimed is:

1. A pharmaceutical composition, comprising a compound of formula I,

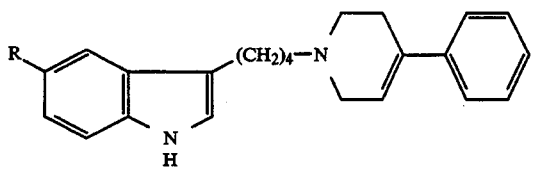

wherein R is OH or COOH,
or a physiological acceptable salt thereof, embedded in pregelatinized starch.

2. The pharmaceutical formulation according to claim 1, wherein R is OH.

3. The pharmaceutical composition according to claim 1, wherein R is COOH.

4. The pharmaceutical composition of claim 1, which is a tablet or capsule.

5. The pharmaceutical composition of claim 1, comprising 0.1-5% by weight of the compound of formula I and 70-99.9% by weight of the pregelatinized starch.

6. The pharmaceutical composition of claim 1, further comprising 0-29.9% by weight of an adjunct.

7. A method of treating a patient having a hypotensive or psychiatric disorder, comprising administering to the patient an effective amount of a pharmaceutical composition according to claim 1.

8. A method of treating a patient having a dopaminergic disorder comprising administering to the patient an effective amount of a pharmaceutical composition according to claim 1.

* * * * *